(12) United States Patent
Law et al.

(10) Patent No.: US 8,328,748 B2
(45) Date of Patent: Dec. 11, 2012

(54) OFF-AXIS BLOOD CHAMBER

(75) Inventors: Perry N. Law, Kaysville, UT (US); Louis L. Barrett, West Point, UT (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 93 days.

(21) Appl. No.: 12/880,519

(22) Filed: Sep. 13, 2010

(65) Prior Publication Data

US 2012/0065568 A1    Mar. 15, 2012

(51) Int. Cl.
*A61M 37/00* (2006.01)

(52) U.S. Cl. ...................................... 604/4.01; 604/6.08

(58) Field of Classification Search .................. 604/4.01, 604/5.01, 6.08, 6.15
See application file for complete search history.

(56) References Cited

U.S. PATENT DOCUMENTS

| | | | | |
|---|---|---|---|---|
| 2,357,238 A * | 8/1944 | Trimble | ........................ | 607/92 |
| 4,243,883 A * | 1/1981 | Schwarzmann | ............... | 250/343 |
| 4,444,498 A * | 4/1984 | Heinemann | ................... | 356/246 |
| 5,351,686 A | 10/1994 | Steuer et al. | | |
| 5,372,136 A | 12/1994 | Steuer et al. | | |
| 5,456,253 A * | 10/1995 | Steuer et al. | ................... | 600/322 |
| 5,458,566 A * | 10/1995 | Herrig et al. | ................... | 604/6.15 |
| 5,769,815 A * | 6/1998 | Utterberg | ......................... | 604/80 |
| 6,069,687 A * | 5/2000 | Briggs | ............................... | 356/39 |
| 6,090,061 A * | 7/2000 | Steuer et al. | ................... | 604/4.01 |
| 6,510,330 B1 * | 1/2003 | Enejder | ......................... | 600/322 |
| 6,554,788 B1 * | 4/2003 | Hunley et al. | ................. | 604/4.01 |
| 6,746,415 B1 * | 6/2004 | Steuer et al. | ................... | 604/4.01 |
| 7,361,267 B2 * | 4/2008 | Delnevo | ......................... | 210/85 |
| 7,671,974 B2 * | 3/2010 | O'Mahony et al. | ............. | 356/39 |
| 2003/0070969 A1 * | 4/2003 | Muller et al. | ................... | 210/91 |
| 2010/0113891 A1 * | 5/2010 | Barrett et al. | ................. | 600/301 |

OTHER PUBLICATIONS

ScienceStockroom Flow Through Cuvette, p. 8/14.*
Blood Chamber 2001—Admitted Prior Art.
CL Photo 2000—Admitted Prior Art.
Blood Chamber Instruction Sheet 2001—Admitted Prior Art.

* cited by examiner

*Primary Examiner* — Leslie Deak
*Assistant Examiner* — Benjamin Klein
(74) *Attorney, Agent, or Firm* — Leydig, Voit & Mayer, Ltd.

(57) ABSTRACT

An extracorporeal blood chamber for an optical blood monitoring system has a mixing area and viewing area that are offset from the axis of the blood flow path into and out of the blood chamber. A flow guide structure redirects an entirety of the flow of blood in a direction substantially orthogonal to the axis and into the viewing area.

7 Claims, 8 Drawing Sheets

OFF-AXIS BLOOD CHAMBER

FIELD OF THE INVENTION

The invention relates to optical blood monitoring systems, and in particular, single-use blood chambers for the real-time measurement of hematocrit and/or oxygen saturation levels. The blood chambers are particularly useful when monitoring a patient during hemodialysis.

BACKGROUND AND SUMMARY

Patients with kidney failure or partial kidney failure typically undergo hemodialysis treatment in order to remove toxins and excess fluids from their blood. To do this, blood is taken from a patient through an intake needle or catheter which draws blood from a blood vessel located in a specifically accepted access location (for example, a shunt surgically placed in an arm, thigh, subclavian, etc.). The needle or catheter is connected to extracorporeal tubing that is fed to a peristaltic pump and then to a dialyzer which cleans the blood and removes excess water. The cleaned blood is then returned to the patient through additional extracorporeal tubing and another needle or catheter. Sometimes, a heparin drip is located in the hemodialysis loop to prevent the blood from coagulating. By way of background, as the drawn blood passes through the dialyzer, it travels in straw-like tubes within the dialyzer which serve as semi-permeable passageways for the unclean blood. Fresh dialysate solution enters the dialyzer at its downstream end. The dialysate surrounds the straw-like tubes and flows through the dialyzer in the opposite direction of the blood flowing through the tubes. Fresh dialysate collects toxins passing through the straw-like tubes by diffusion and excess fluids in the blood by ultra filtration.

It is known in the art to use an optical blood monitoring system during hemodialysis, such as the CRIT-LINE® monitoring system which is sold by the assignee of this application. This blood monitoring system uses optical techniques to non-invasively measure in real-time the hematocrit level of blood flowing through a hemodialysis system. In this system, a sterile, single-use blood chamber is preferably attached in-line to the extracorporeal tubing on the arterial side of the dialyzer. The blood chamber provides a viewing point for optical sensors during the hemodialysis procedure. Multiple wavelengths of visible and infrared light are directed through the blood chamber and the patient's blood flowing therethrough, and a photodetector detects the resulting intensity of each wavelength. The preferred wavelengths are about 810 nm (e.g. 829 nm), which is substantially isobestic for red blood cells, and about 1300 nm, which is substantially isobestic for water. A ratiometric technique implemented in the corresponding controller, substantially as disclosed in U.S. Pat. No. 5,372,136 entitled "System and Method for Non-Invasive Hematocrit Monitoring", which issued on Dec. 13, 1999 and is assigned to the assignee of the present application, uses this information to calculate the patient's hematocrit value in real-time. The hematocrit value, as is widely used in the art, is the percentage determined by dividing the volume of the red blood cells in a given whole blood sample by the overall volume of the blood sample. The system can also measure, optically, the oxygen saturation level in the blood flowing into the dialyzer. The preferred wavelength for measuring oxygen saturation levels are about 660 nm and about 810 nm.

In a clinical setting, the actual percentage change in blood volume occurring during hemodialysis can be determined, in real-time, from the change in the measured hematocrit. Thus, an optical blood monitor, such as the CRIT-LINE® monitor, is able to non-invasively monitor not only the patient's hematocrit level but also the change in the patient's blood volume in real-time during a hemodialysis treatment session. The ability to monitor real-time change in blood volume facilitates safe, effective hemodialysis and patient fluid management.

The blood chamber used in the current system comprises a molded body made of clear medical grade polycarbonate. The chamber body along with the tube set are replaced for each patient at each treatment. As mentioned, the blood chamber is normally attached in line to the extracorporeal tubing on the arterial side of the dialyzer. The most common area to experience leaks is where the blood chamber seats onto the dialyzer.

The blood chamber provides a flat and generally circular, internal blood flow cavity, as well as two circular viewing lenses: one being integrally molded with the body of the polycarbonate blood chamber and the other being welded into place into the body. The distance between the blood chamber lenses must be constant and maintained within the tight tolerances in manufacturing for calibration to be accurate and repeatable. An inlet port and channel communicate through a first opening into the flat and generally circular internal blood flow cavity, and the outlet port and channel communicate through a second opening. The first port and channel and second port and channel are in axial alignment through the diameter of the internal blood flow cavity. The inlet port is can be bonded to a tube set or terminate in a luer lock fitting, whereas the outlet port includes a fitting such as a luer lock type fitting intended for connection to a dialyzer blood filter. The attendant must be careful to properly seat the luer lock fitting on the port for the arterial side of the dialyzer in order to avoid leaking. The photoemitters and photodetectors for the optical blood monitor are clipped into place on the blood chamber over the lenses. The blood chamber is molded with a moat around the flat viewing region in the blood flow cavity between the viewing lenses. The moat holds a relatively thick layer of blood, and helps to attenuate ambient light and light piping inaccuracies.

The state of the flow of blood through the viewing area is quite important in order to obtain accurate, robust measurements. Laminar flow is not typically desirable. For this purpose, present day blood chambers include posts upstream of the viewing area to create eddy currents and mix the blood. This is more important at low velocities than at high velocities. Even though it is important to mix the blood and maintain homogeneity as it flows through the blood chamber, it is also important that the flow through the blood chamber not create hemolysis (i.e., rupture blood cells).

SUMMARY OF THE INVENTION

In accordance with the invention, the blood chamber is designed with a viewing area that is off-axis from the blood flow path, rather than located centrally along the flow axis as in prior art. The off-axis design enables the body of the blood chamber to provide more leverage and torque with less effort when the blood chamber is turned to be seated on the dialyzer. The improved leverage helps to eliminate leaks by allowing the attending staff to tighten the connection with less physical effort.

The internal blood flow cavity is defined by two substantially parallel internal flat walls separated by a predetermined distance. The viewing area within the internal blood flow cavity is defined by a pair of viewing lenses that are commensurate with at least a portion of the parallel flat walls defining the internal blood flow cavity. A first port and channel, e.g. an inlet port and channel, communicate within the flat, internal blood flow cavity, as do a second port and channel, e.g. outlet port and channel. The first port and channel and the second port and channel are generally in axial alignment with each other along a first axis, however, in accordance with the invention, the viewing region is offset from the first axis.

Preferably, a pair of flow guides is located within the internal blood flow cavity. The first flow guide guides blood flowing into the internal blood flow cavity such that the blood flow is redirected off the first axis and into the viewing region. The second flow guide guides blood exiting from the viewing region such that it flows efficiently through the outlet port and channel to exit the blood chamber. Preferably, the shape of the flow guides, as well as the internal blood flow cavity, is symmetric with respect to the direction of the flow of the blood. This feature allows the blood chamber to be used in either direction when connected to the extracorporeal tubing and dialyzer, which is particularly useful in applications where it may not be desirable to affix the blood chamber to the extracorporeal tubing set via adhesive prior to commercial distribution. In the prior art blood chamber using a turbulence post at the upstream end of the internal blood flow cavity, care must be taken to ensure that the blood chamber is oriented in the proper direction to locate the turbulence posts upstream of the blood flow cavity. In the preferred embodiment of the present invention, this concern is not an issue. The flow guides create an eddy current around the viewing area in a circular fashion thereby causing continual mixing and homogeneity in the blood being measured. The output flow guide diverts blood from the circulating current out the output port.

In a preferred embodiment of the invention, the lenses on the chamber body provide a circular viewing region, preferably having the same dimensions as in the prior art blood flow chambers. Consistency of dimension and materials may allow use of the same sensor clip assembly as with the prior art blood chambers. As will be apparent in the following drawings, the internal blood flow cavity is defined in part by a peripheral wall spanning between the flat parallel walls of the internal blood flow cavity. It is preferred that this peripheral wall be arcuate in order to foster efficient and complete flow of blood through the internal blood flow cavity, and also that the peripheral wall have a radius greater than the radius of the circular viewing region. It has been found that this configuration provides a robust, thoroughly mixed and consistent flow through the circular viewing area, without any significant amount of hemolysis as it flows through the blood chamber.

In addition to the above features, a blood chamber constructed in accordance with the invention is also well suited to implement aspects of the invention disclosed in co-pending patent application entitled "Blood Chamber For An Optical Blood Monitoring System", by Louis Barrett and Perry Law, filed on even date herewith, Ser. No. 12/876,572, assigned to the assignee of the present invention and incorporated herein by reference. More specifically, the viewing lenses are made of a clear material, such as clear medical grade polycarbonate (polished), in order to facilitate the emission and detection of light and infrared radiation at the predetermined wavelengths, e.g. at about 660 nm, 810 nm, and 1300 nm, passing through the viewing lenses and the blood flowing through the viewing region in the internal blood flow cavity. At least a portion of the blood chamber, however, is made of a material that is opaque to light at the 660 nm wavelengths such as a blue-tinted material. The purpose of the blue-tinted opaque blood chamber is to eliminate light ducting errors in the measurement of oxygen saturation levels at low SAT values and low HCT values. Preferably, the entire chamber body is made of an opaque material, and each of the pair of lens bodies is made of a clear, transparent material which are sonically welded to the chamber body to form the blood chamber.

Other objects and advantages of the invention will be apparent to those skilled in the art upon reviewing the following drawings and description thereof.

DETAILED DESCRIPTION

Prior Art

Figure 1:
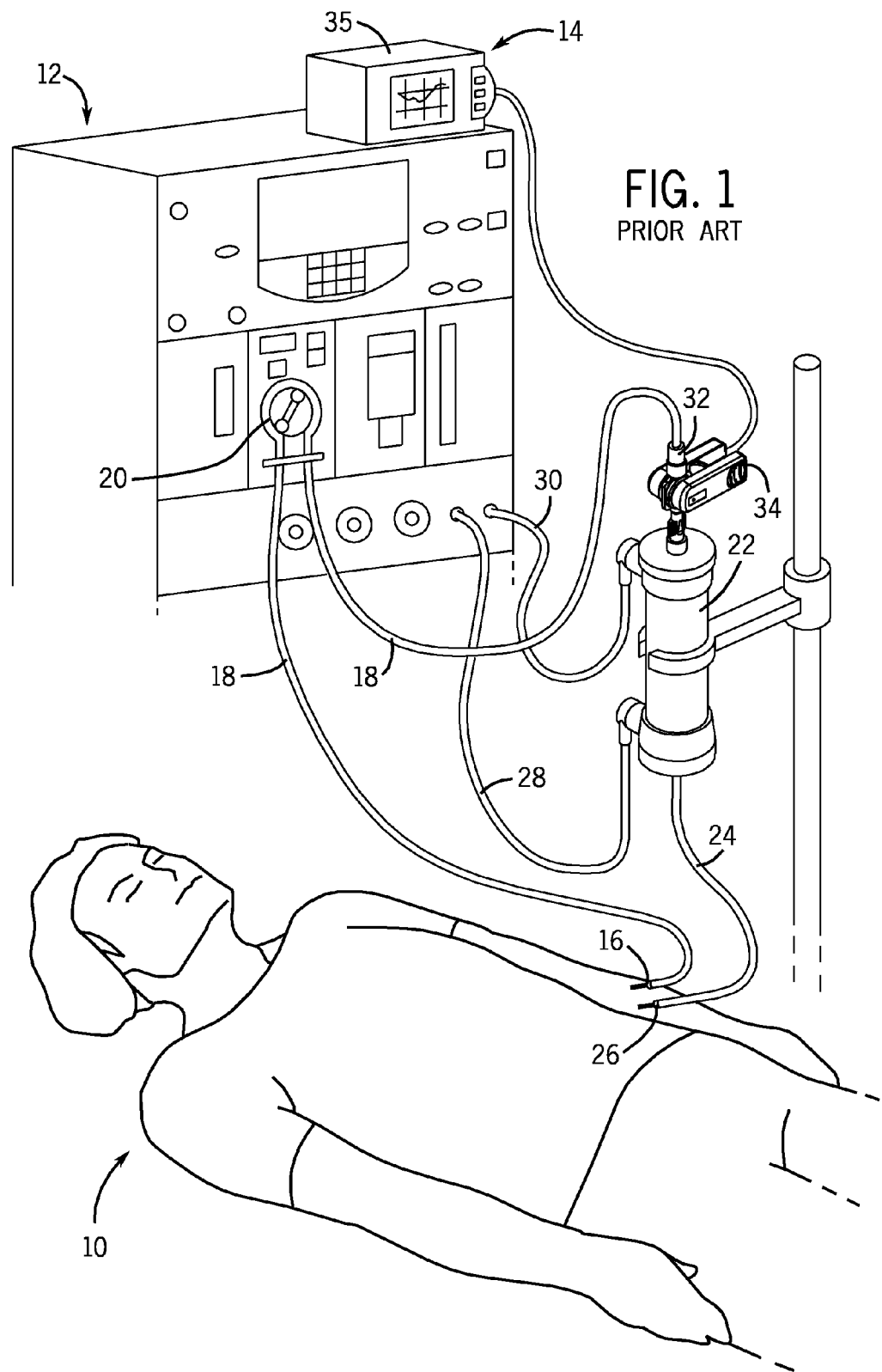
FIG. 1 is a perspective view of a patient undergoing hemodialysis treatment with a non-invasive, optical blood monitor monitoring the patient's blood in real-time as it passes through extracorporeal tubing in the hemodialysis system.

FIG. 1 illustrates a patient 10 undergoing hemodialysis treatment with a conventional hemodialysis system 12, and also illustrates a non-invasive, optical blood monitor 14. A typical hemodialysis clinic will have several hemodialysis systems 12 for treating patients.

An input needle or catheter 16 is inserted into an access site of the patient 10, such as shunt in the arm, and is connected to extracorporeal tubing 18 that leads to a peristaltic pump 20 and then to a dialyzer or blood filter 22. The dialyzer 22 removes toxins and excess fluid from the patient's blood. The dialysized blood is returned from the dialyzer 22 to the patient through extracorporeal tubing 24 and a return needle or catheter 26. The extracorporeal blood flow normally receives a heparin drip to prevent clotting although that is not shown in FIG. 1. Excess fluids and toxins are removed by clean dialysate liquid which is supplied to the dialyzer 22 via tube 28 and removed for disposal via tube 30. A typical hemodialysis treatment session in the United States takes about 3 to 5 hours.

The optical blood monitor 14 includes a blood chamber 32, a sensor clip assembly 34, and a controller 35. The blood chamber 32 is preferably located in line with the extracorporeal tubing 18 upstream of the dialyzer 22. Blood from the peristaltic pump 20 flows through the tubing 18 into the blood chamber 32. The preferred sensor assembly 34 includes LED photoemitters that emit light at substantially 810 nm (e.g. 829 nm), which is isobestic for red blood cells, substantially 1300 nm, which is isobestic for water, and at substantially 660 nm, which is sensitive for oxygenated hemoglobin. The blood chamber 32 includes lenses so that the sensor emitters and detector(s) can view the blood flowing through the blood chamber 32, and determine the patient's real-time hematocrit value and oxygen saturation value using ratiometric techniques generally known in the prior art, See, U.S. Pat. No. 5,372,136.

Figure 2:
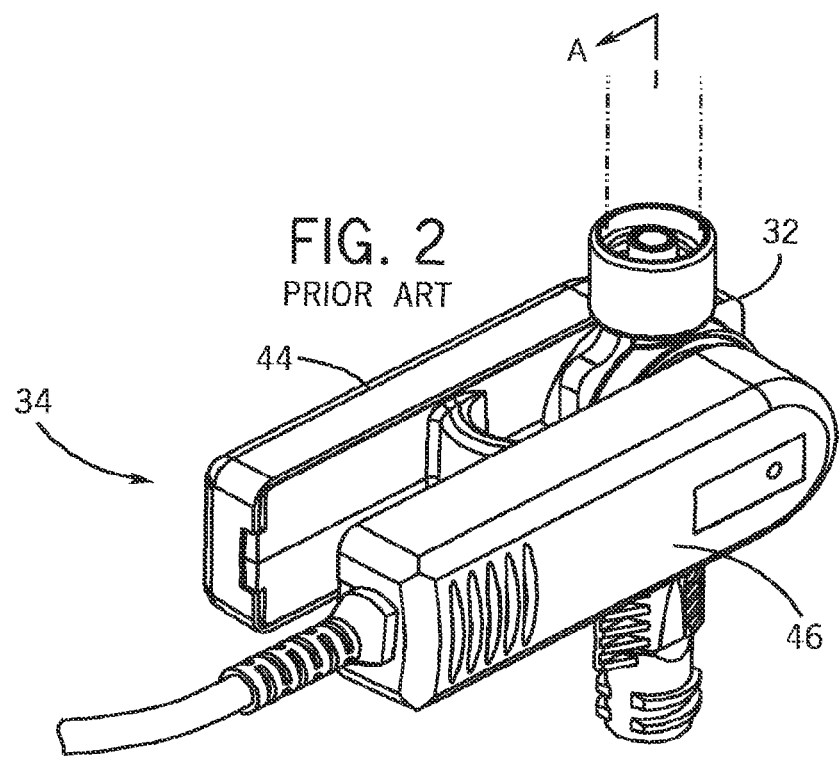
FIG. 2 is a perspective view showing a sensor assembly for the optical blood monitor positioned to sense blood flowing through a prior art blood chamber connected in the extracorporeal tubing of the hemodialysis system.
Figure 3:
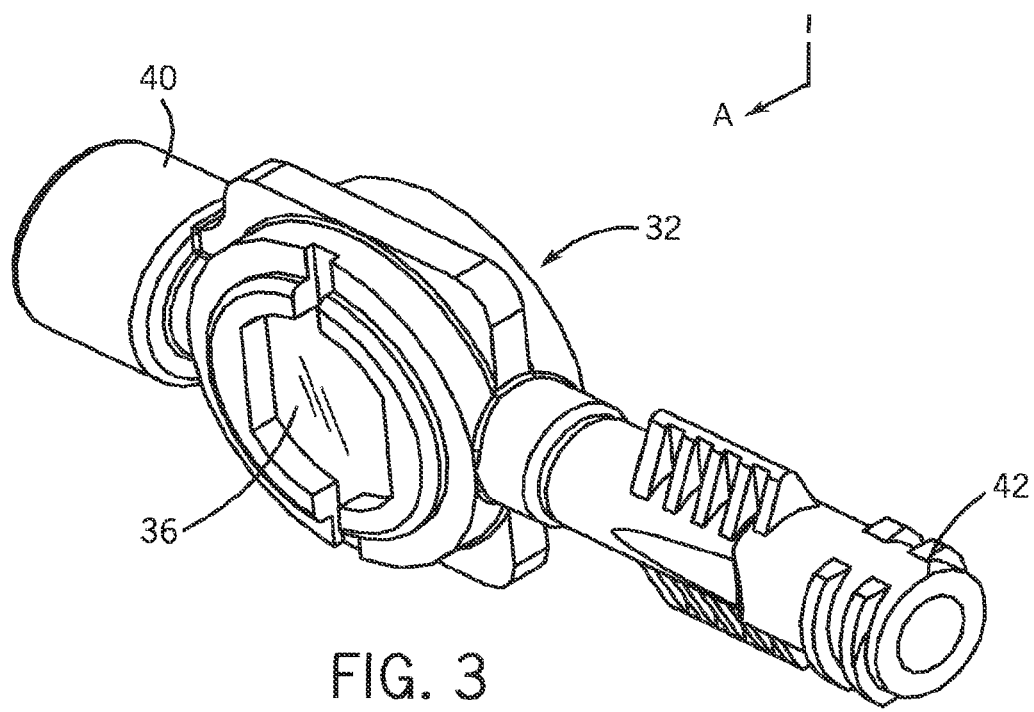
FIG. 3 is a perspective view of the prior art blood chamber shown in FIG. 2.
Figure 4:
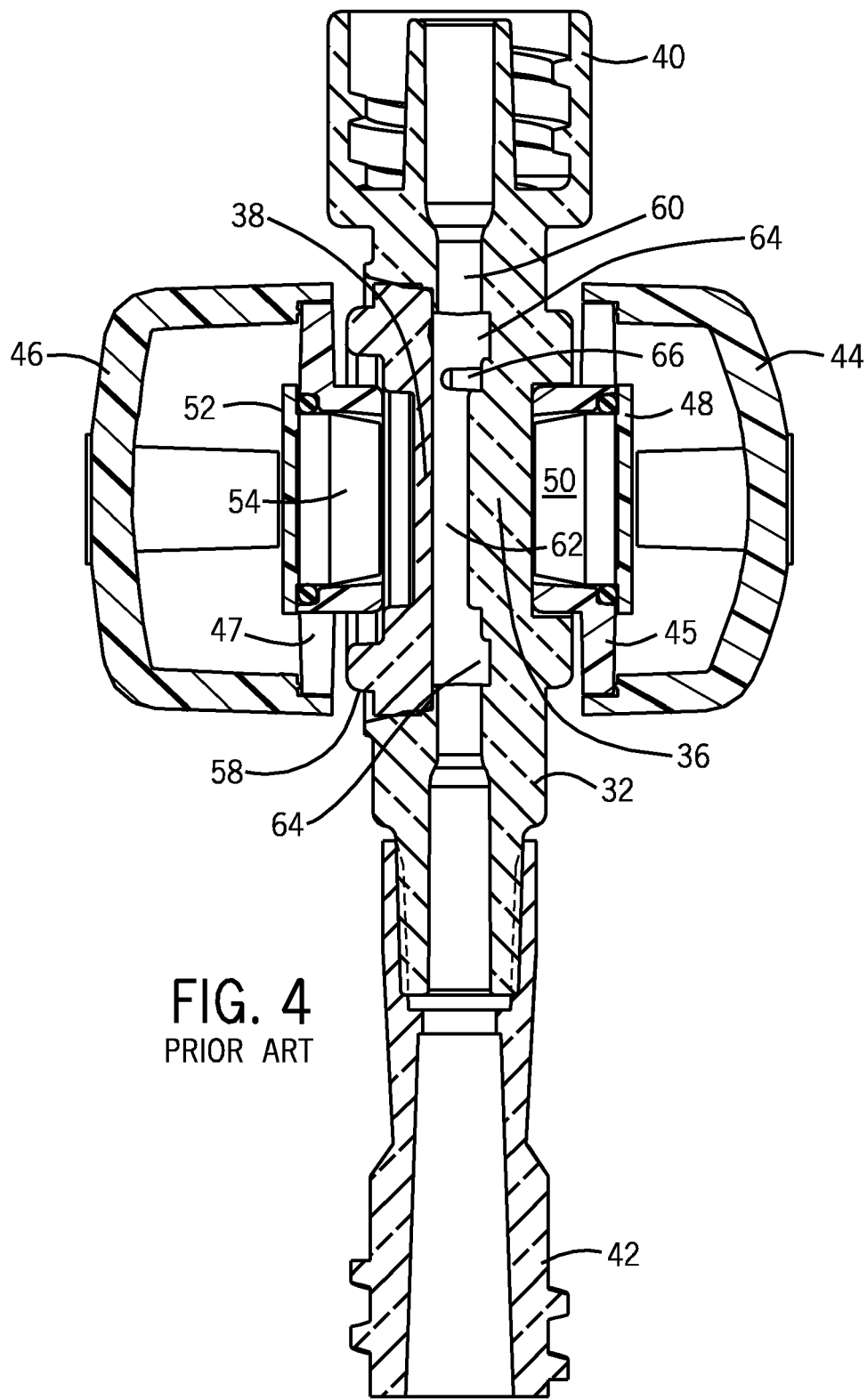
FIG. 4 is a cross-sectional view of the prior art blood chamber taken along line A-A in FIG. 2.

Referring to now FIGS. 2-4, the body of a prior art blood chamber 32 is made of molded, medical grade, clear polycarbonate. It includes two viewing windows 36, 38 (see FIG. 4). The inlet 40 and outlet 42 are designed to be compatible with standard medical industry connecting devices, conventionally known as luer lock connectors. In the blood chamber 32 shown in FIGS. 2-4, the inlet 40 is integrally molded with the blood chamber 32, whereas the outlet 42 consists of a suitable off-the-shelf connection adapter bonded to the body of the blood chamber 32. The sensor assembly 34 includes an emitter subassembly 44 and a detector subassembly 46. As best shown in FIG. 4, an emitter circuit board 48 containing LEDs emitting light and infrared radiation at substantially 660 nm, 810 nm and 1300 nm is mounted within the housing for the emitter subassembly 44. The photoemitters on the LED circuit board 48 emit light through a molded lens 50 that mounted in the housing of the emitter subassembly 44, and direct radiation through the viewing window 36 for the blood chamber 32. Another circuit board 52 contains detectors, one made of silicon to detect intensity at 660 nm and 810 nm, and the other made of Indium Gallium Arsenide (InGaAs) to detect intensity at 1300 nm. The detector circuit board 52 is mounted within the housing for the detector subassembly 46. A molded lens 54 over the detectors 52 is also mounted into subassembly 46. The viewing window 38 in the blood chamber 32 facilitates transmission of light and infrared radiation at the respective wavelengths to the detectors on the chip 52 of the detector subassembly 46. The controller 35 (FIG. 1), controls the operation of the each of the respective LED emitters and detector(s) in order to multiplex the independent wavelength measurements so only one emitter is active at any given moment in time. Note that the viewing window 38 is molded as part of a separate insert 58 (referred to as the lens body 58) that is sonically welded to the body of the blood chamber 32. Blood flows from the inlet 40 through the passageway 60 to a central viewing region 62 in an internal blood flow cavity 62. The internal blood flow cavity provides a substantially flat, thin (e.g. less than 0.1 inches) viewing region for the blood flowing through the blood chamber 36. The pulses of light or infrared radiation at the three selected wavelengths, namely 810 nm, 1300 nm and 660 nm, are transmitted through the blood flowing through the flat viewing region provided by internal blood flow cavity 62, as well as through the viewing windows 36, 38. A moat 64 that is somewhat deeper than the flat viewing region 62 surrounds the flat viewing region 62. The moat 64 serves two primary purposes. The moat distributes non-laminar flow evenly and steadily through the viewing region. As explained in the above referenced co-pending patent application, it has been discovered that the moat also provides a thicker region of blood which under normal conditions optically isolates the detectors from ambient light and light ducting from the photoemitters through the chamber body without passing through the blood flowing through the viewing region. The use of the moat 64 to prevent light ducting is not particularly effective at low hematocrit values, especially at the 660 nm wavelength that is important for monitoring oxygen saturation levels. One or more turbulence posts 66 are located immediately upstream of the viewing region 62 to create steady eddy currents in the flow across the viewing region 62. While the flow through the viewing region 62 is non-laminar, the configuration of the blood chamber 32 shown in FIG. 4 results in steady flow through the viewing region 62 in terms of pressure and flow rate.

The housings 44 and 46 for the sensor assembly 34 include an inner housing frame 45, 47 which connects to the outer shells 44, 46. The inner housing frames 45, 47 provide an opening into which the molded lenses 50, 54 are mounted. The sensor assembly 34 is preferably a spring-loaded clip assembly adapted to be removably mounted to the blood chamber 32, as shown in FIGS. 2 and 4. Both sides of the blood chamber 32 are molded such that the clip 34 will reside in a predetermined position when mounted to the blood chamber 32. As mentioned, blood chamber 32 is a single-use clear polycarbonate component. Between patients, the blood chamber 32 is replaced along with the extracorporeal tubing 18 and 24.

Figure 5:
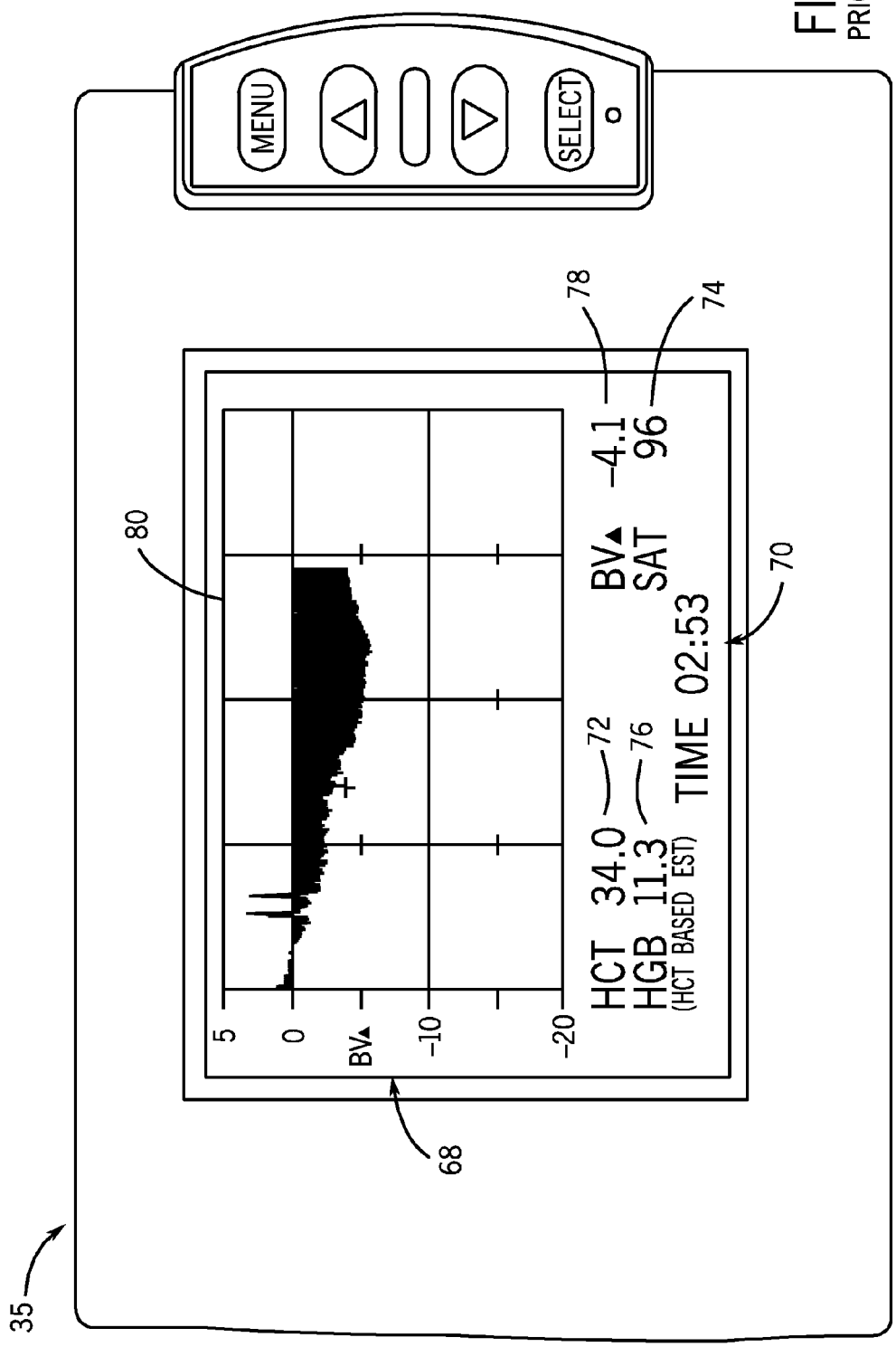
FIG. 5 is a front elevational view of a controller for the optical blood monitor displaying data including real-time hematocrit (HCT), change in blood volume (BVΔ), hemoglobin (HBG), and oxygen saturation (SAT) levels, as well as the amount of time into the hemodialysis treatment session and a graphical representation of the change in blood volume during the course of the hemodialysis treatment session.

FIG. 5 is a front elevational view of the controller 35 for the optical blood monitor 14. The controller 35 includes a display 68 to provide real-time blood monitoring data for the patient undergoing hemodialysis. The display in FIG. 5 illustrates the amount of time 70 that the patient 10 has been undergoing hemodialysis for the current treatment session. The time 70 displayed on the screen 68 in FIG. 5 is 2 hours and 53 minutes. The display 68 also illustrates real-time values for the optically monitored hematocrit (HCT) 72 and oxygen saturation (SAT) level 74, as well as the calculated values for hemoglobin (HGB) 76 and change in blood volume (BVΔ) during the treatment session 78. The graph 80 on the display 68 illustrates the change in the patient's blood volume over the course of the 2 hour and 53 minute treatment session. This data is typically displayed, as shown in FIG. 1, in a location that is located within the vicinity of the patient 10.

Periodically, the calibration and accuracy of the optical blood monitor 14 should be checked. In the art, this is normally done by placing the sensor clip 34 onto a verification filter (made of layered plastic having known optical qualities) that is mounted to the side of the controller 35. Calibration software within the controller 35 verifies the calibration of the unit, or allows the user to field calibrate the unit to bring it back to factory calibration settings. In some instances, it may be necessary to return the unit to the factory for calibration.

Present Invention

Figure 7:
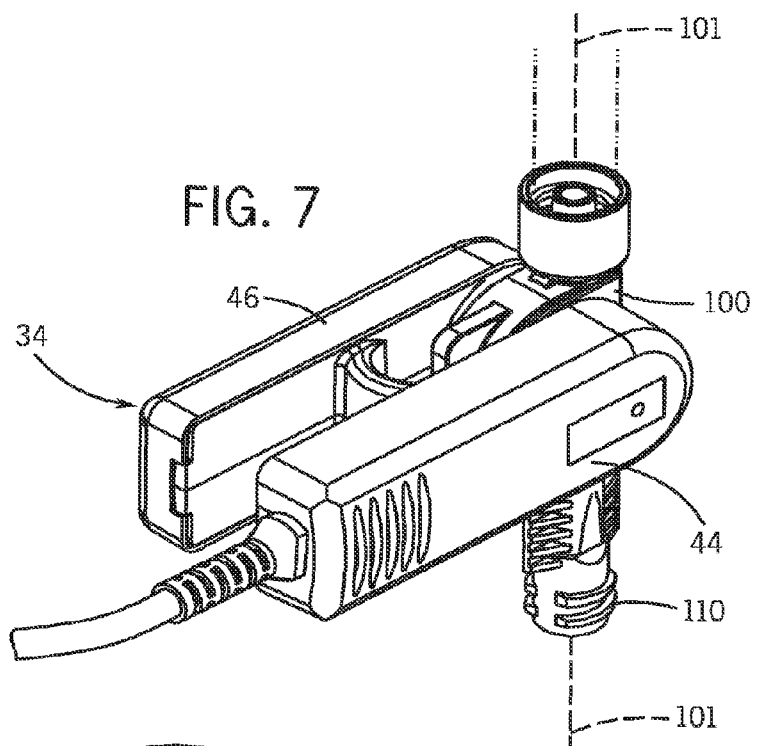
FIG. 7 is a perspective view showing a sensor assembly for an optical blood monitor positioned to sense optical characteristics of blood flowing through a blood chamber constructed in accordance with the invention.
Figure 6:
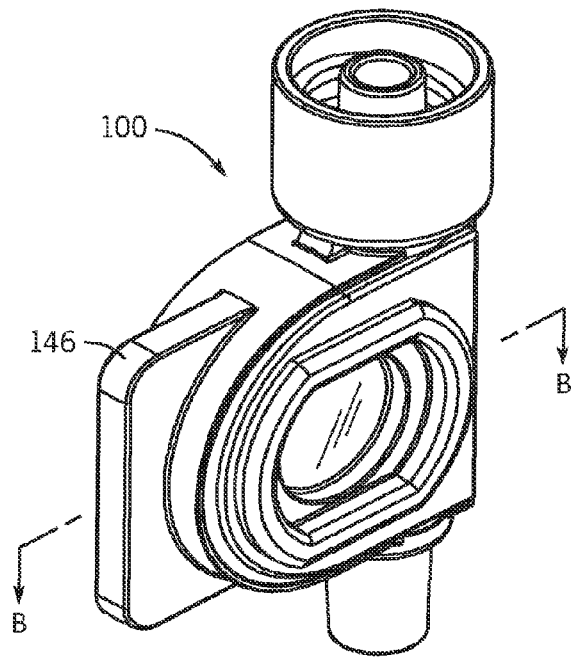
FIG. 6 is a perspective view of the blood chamber constructed in accordance with the invention.
Figure 8:
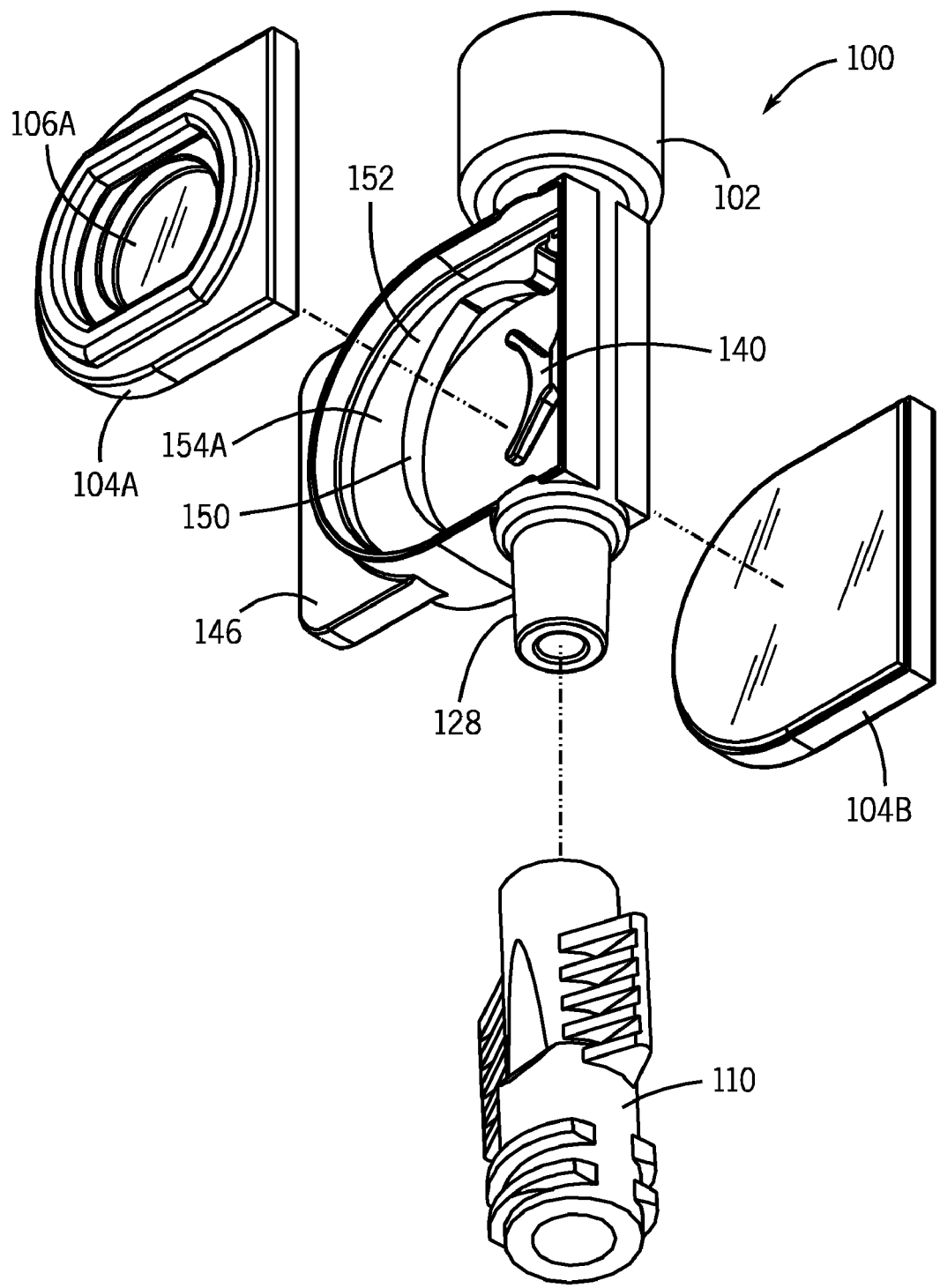
FIG. 8 is an exploded view of the blood chamber illustrated in FIG. 6.

FIGS. 6 through 11 illustrate a blood chamber 100 constructed in accordance with a preferred embodiment of the invention, in which the internal blood flow cavity 120 and viewing area is offset from the axis 101, FIG. 7, of blood flow through the extracorporeal tubing. Referring in particular to FIG. 8, the blood chamber 100 is constructed by sonically welding two lens bodies 104A and 104B to the chamber body 102. In addition, a luer lock type adapter 110 is bonded to port 128 on the chamber body 102. The chamber body 102 may be molded from opaque polycarbonate material as described in the incorporated, co-pending patent application entitled "Blood Chamber For an Optical Blood Monitoring System", although most aspects of the invention may be implemented with a clear polycarbonate chamber body 102. The lens bodies 104A, 104B are preferably made of molded clear polycarbonate material and each includes a viewing lens 106A, 106B. In use, the luer lock fitting 110 attaches to the dialysis filter. The offset configuration for the blood chamber 102 provides greater leverage for twisting the blood chamber 102 and luer lock fitting 110 into place on the dialysis filter than with the prior art blood chambers.

Figure 9:
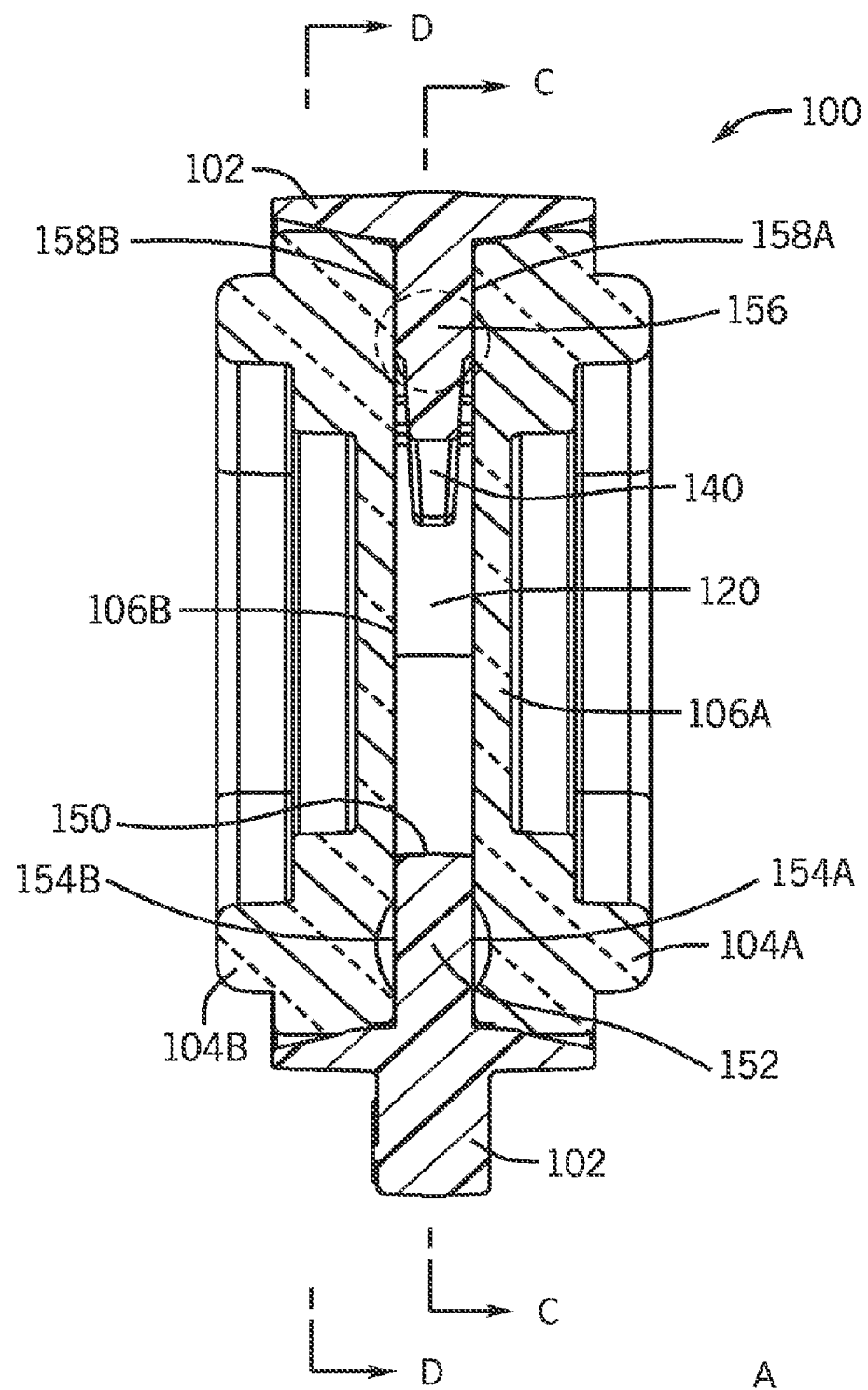
FIG. 9 is a sectional view taken along line B-B in FIG. 6.
Figure 10:
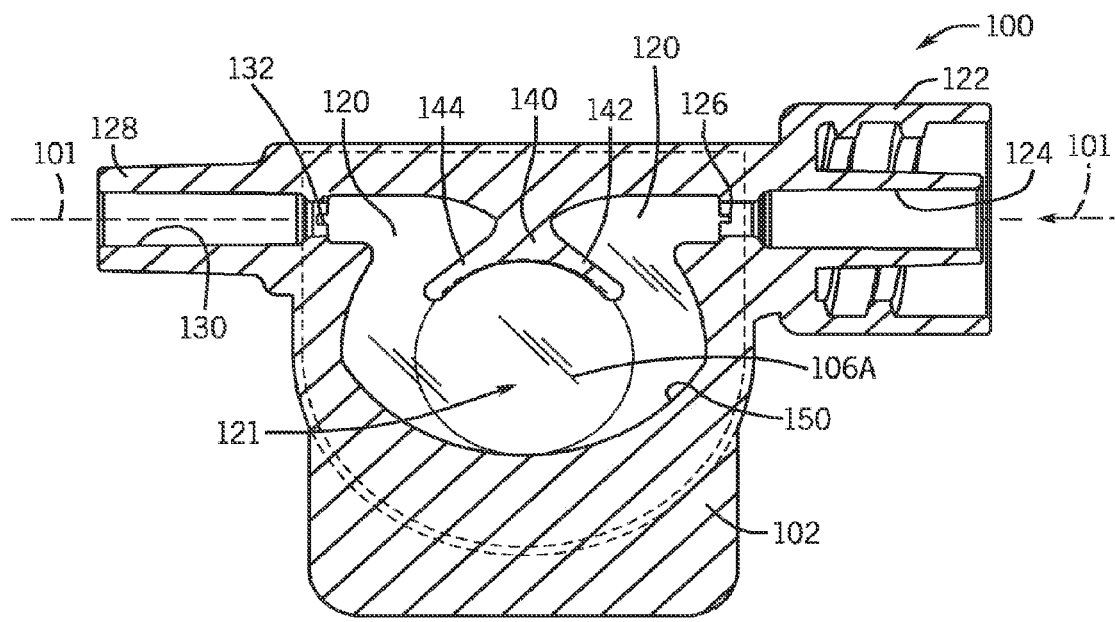
FIG. 10 is a sectional view taken along line C-C in FIG. 9.

Referring now in particular to FIG. 10, the blood chamber 100 includes a first port 122 and channel 124 that are in fluid communication with an internal blood flow cavity 120 through an opening 126. The blood chamber 100 also includes a second port 128 and channel 130 that are in fluid communication with the internal blood flow cavity 120 through opening 132. The flow path through the first port 122 and channel 124 is in general axial alignment with the flow through the second channel 130 and port 128. This axis of flow is shown in phantom in FIGS. 7 and 9 and is labeled with reference number 101. Blood flow, once inside the blood chamber 100, is diverted off-axis into the internal blood flow cavity 120. The chamber body 102 includes a flow guide structure 140 comprising a first guide 142 and a second guide 144. The first guide 142 guides the flow of blood from the first port 122 and channel 124 flowing into the internal flow cavity 120 off axis to a mixing and viewing region 121 within the internal flow cavity 120. As shown in FIG. 10, the first flow guide 142 preferably redirects the flow of blood in a serpentine flow path, which has been found to provide robust, non-laminar and fully mixed blood flow in the viewing area 121 without the use of turbulence post. The second guide 144 guides blood flow from the viewing area 121 again along a serpentine flow path back into general axial alignment along flow axis 101 in order to exit through the second channel 130 and port 128. The shape of the flow guides 142 and 144, as well as the shape of the internal blood flow cavity 120, is symmetric with the direction of the flow of blood. As mentioned, this enables the blood flow chamber 100 to be bi-directional and avoids concerns that the blood flow chamber may be reversed when connected in line for use.

Figure 11:
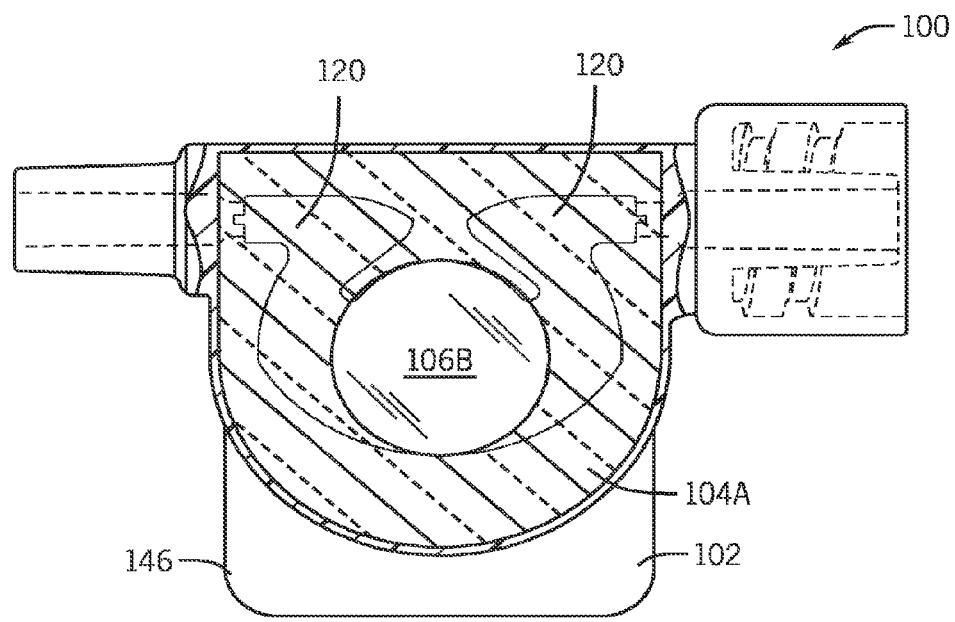
FIG. 11 is a sectional view taken along line D-D in FIG. 9.

The flat blood flow cavity 120 is defined in part by an arcuate peripheral wall 150 on the chamber body 102. The arcuate wall 150 spans between the flat parallel walls of the lens bodies 104A, 104B when the blood chamber 100 is fully assembled. The radius of the arcuate peripheral wall 150 is greater than the radius of the circular viewing region 121. As depicted in FIG. 11, the circular viewing area 106B through the lens body 104B is somewhat smaller than the overall area of the internal flow cavity 120. The radius of the circular viewing region 121 is preferably the same as in the prior art blood chambers so that the same sensor clip assemblies 34 may be used with the blood chamber 100 made in accordance with the invention, as with the blood chamber 32 made in accordance with the prior art. It has been found that the configuration of the serpentine inlet and outlet flow path along with the relatively larger radiused peripheral wall 150 for the internal flow cavity provide a consistent, robust, non-laminar flow across the circular viewing area 121.

Referring now to FIGS. 8 and 9, the peripheral wall 150 on the chamber body 102 resides at the edge of an inwardly extending shelf 152. The shelf 152 includes two parallel mounting surfaces 154A, 154B. In a similar fashion, the base 156 of the flow guide structure 140 includes mounting surfaces 158A, 158B. The mounting surfaces 154A and 158A reside in a parallel plane, as do the mounting surfaces 154B and 158B. As shown in FIGS. 8 and 9, the respective internal walls of the lens bodies 104A, 104B are flat, and much larger than the respective circular viewing areas 106A, 106B. The outer edges of the internal flat surfaces of the lens bodies 104A, 104B are sonically welded to the respective mounting surfaces 154A, 158A and 154B and 158B on the chamber body 102. Alternatively, medical grade bonding material can be used to attach the lens bodies 104A, 104B. In any event, it is important to attach the lens bodies 104A, 104B in a manner that prevents leaking. It is also important that the distance across the internal flow cavity 120 be maintained at a consistent and precise distance correlating to the calibration of the sensor clip assembly 34. As mentioned, it is preferred that the dimensions across the internal flow cavity 120 be the same as in the prior art blood chambers.

The chamber body 102 also includes a flange 146 that extends outward from the chamber body 102 radially away from the longitudinal flow axis 101. The flange 146 provides a convenient gripping location for the user when installing the blood chamber 102. Its location being extended away from the flow axis 101 provides additional leverage for twisting or torquing the blood chamber 100 into place on the dialysis filter.

The chamber body 102 in FIG. 10 is shaded as an opaque material to signify that it is made from a blue-tinted material in order to isolate the viewing lenses from light ducting at 660 nm from one lens 106A to the other lens 106B without passing directly through blood flowing through the internal blood flow chamber 120, 121. Turning briefly to FIG. 11, the lens bodies 104B are made of a clear material as depicted by the shading in FIG. 11, yet the opaque nature of the chamber body 102 and its configuration serves to isolate the viewing lenses 106A, 106B from light ducting as described in the above incorporated, co-pending patent application entitled "Blood Chamber For An Optical Blood Monitoring System". Preferably, the parameters relating to the optical characteristics of the blood chamber 100, namely, the material and thickness of the optical lenses 106A, 106B the distance across the internal blood flow chamber and the mixing area 121 between the lenses 106A and 106B as well as the distance between photoemitters and detectors mounted to the blood chamber 100 are consistent with that of the prior art blood chamber described earlier.

The described use and embodiment of the invention is to be considered in all respects as only illustrative and not restrictive.

What is claimed is:

1. A blood chamber for optically monitoring blood flowing through an extracorporeal tube, the blood chamber defining a flow path through an internal blood flow cavity which provides a viewing area for optical monitoring of the blood, the blood chamber comprising:
    an internal blood flow cavity disposed between two substantially parallel internal flat walls separated by a predetermined distance;
    a first port and channel in fluid communication with the internal blood flow cavity;
    a second port and channel in fluid communication with the internal blood flow cavity,
    the first port and channel and the second port and channel being in axial alignment along a first axis;
    a viewing area within the internal blood flow cavity defined by a pair of viewing lenses aligned with at least a portion of the respective flat walls defining the internal blood flow cavity, the viewing region being entirely offset from the first axis;
    external surfaces of the flat walls each including features configured to mate to complementary features on surfaces of an optical sensor assembly in order to enable attaching the sensor assembly and the blood chamber; and
    a flow guide structure in the internal blood flow cavity configured to redirect an entirety of the flow of blood in a direction substantially orthogonal to the first axis and into the viewing area, where the flow guide structure is symmetrical so as to similarly redirect the flow of blood whether the flow is from the first port to the second port or from the second port to the first port.

2. A blood chamber as recited in claim 1 wherein the flow guide structure includes a pair of flow guides that channel the internal blood flow in a circular pattern to encourage formation of one of more eddy current to promote mixing and homogeneity of the blood in the viewing area.

3. A blood chamber as recited in claim 1 wherein the lenses provide a circular viewing region.

4. A blood chamber as recited in claim 3 further comprising a peripheral wall spanning between the flat parallel walls and defining part of the blood flow cavity, the peripheral wall being arcuate and having a radius greater than the radius of the circular viewing region.

5. A blood chamber as recited in claim 1 wherein the viewing lenses are made of a clear material in order to facilitate the emission and detection of light at predetermined wavelengths passing through the viewing lenses and blood flowing through the viewing region of internal blood flow cavity, and at least a portion of the blood chamber is made of an opaque material, wherein the opaque portion of the blood chamber isolates the viewing lenses from light ducting from one lens to the other lens without passing through blood flowing through the internal blood flow cavity.

6. A blood chamber as recited in claim 5 wherein the blood chamber includes a chamber body made of an opaque material, and a pair of lens bodies each made of a clear material, the lens bodies being sonically welded to the chamber body to form the blood chamber.

7. A blood chamber as recited in claim 6 wherein the lens bodies are molded from clear polycarbonate, and the chamber body is molded from tinted polycarbonate material which does not transmit light energy at or near at least one of 660 nm, 810 nm and 1300 nm.

* * * * *